(12) United States Patent
Collins et al.

(10) Patent No.: US 7,031,770 B2
(45) Date of Patent: Apr. 18, 2006

(54) DISTINGUISHING SINUS TACHYCARDIA FROM ATRIAL FIBRILLATION AND ATRIAL FLUTTER THROUGH ANALYSIS OF ATRIAL CHANNEL WAVELET TRANSFORMS

(75) Inventors: Kevin Collins, Minneapolis, MN (US); Milton M. Morris, Minneapolis, MN (US); Alan F. Marcovecchio, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 287 days.

(21) Appl. No.: 10/334,651

(22) Filed: Dec. 31, 2002

(65) Prior Publication Data

US 2004/0127945 A1    Jul. 1, 2004

(51) Int. Cl.
*A61N 1/39* (2006.01)

(52) U.S. Cl. .......................................................... 607/5
(58) Field of Classification Search ................... 607/5, 607/27; 128/702; 600/515
See application file for complete search history.

(56) References Cited

U.S. PATENT DOCUMENTS

| | | | |
|---|---|---|---|
| 5,379,776 A | 1/1995 | Murphy et al. | |
| 5,404,880 A | 4/1995 | Throne | |
| 5,447,519 A | 9/1995 | Peterson | |
| 5,782,888 A * | 7/1998 | Sun et al. ...................... | 607/27 |
| 5,857,977 A | 1/1999 | Caswell et al. | |
| 6,266,554 B1 | 7/2001 | Hsu et al. .................... | 600/515 |
| 6,393,316 B1 * | 5/2002 | Gillberg et al. ............. | 600/515 |
| 6,438,410 B1 | 8/2002 | Hsu et al. | |
| 2004/0019287 A1 | 1/2004 | White | |

OTHER PUBLICATIONS

Chiang, Chih-Ming J., et al., "Discrimination of Ventricular Tachycardia From Sinus Tachycardia By Antitachycardia Devices: Value of Median Filtering", *Medical Engineering Physics, vol. 16*, (1994),513-517.

Morris, Milton M., et al., "Intracardiac Electrogram Transformation, Morphometric implications for Implantable Devices", *Journal of Electrocardiology*, vol. 29 Supplement, (1996),124-129.

(Continued)

*Primary Examiner*—George Manuel
*Assistant Examiner*—Dana D Green
(74) *Attorney, Agent, or Firm*—Schwegman, Lundberg, Woessner & Kluth, P.A.

(57) ABSTRACT

An implantable heart-monitoring device designed to distinguish two differing heart rhythms. The device comprises electrodes, a template, and first, second and third electronic mechanisms. The first electronic mechanism converts electrical representations of heartbeats from the electrodes into digital data and performs calculations including at least a partial discrete wavelet transform upon the digital data to generate a subset of discrete wavelet transform components including components for distinguishing the two differing heart rhythms and also demonstrated to be relatively low in variability from one patient to another. The template contains a corresponding subset of discrete wavelet transform components captured from at least one individual whose heart was beating in accordance with one of the two differing heart rhythms. The second electronic mechanism correlates the subset of transform components against the template components and provides a correlation value. The third electronic mechanism mathematically examines a time series of the correlation values and gives an indication of whether the first or second of the heart rhythms is present.

51 Claims, 6 Drawing Sheets

OTHER PUBLICATIONS

Olson, Walter H., "Dual Chamber Sensing and Detection for Implantable Cardioverter-Defibrillators", *Chapter 17 of Nanopharmacological Therapy of Arrhythmias for the 21st Century: The State of the Art.*, Futura Publishing Co., Inc., Armonk, N.Y., (1998),385-421.

Schwartz, Mark, et al., "Cardiac Rhythm Management Systems And Methods Using Multiple Morphology Templates For Discriminating Between Rhythms", *U.S. Appl. No. 10/291,200,* (Nov. 8, 2002),42 pgs.

Throne, Robert D., et al., "A Comparison of Four New Time-Domain Techniques for Discriminating Monomorphic Ventricular Tachycardia from Sinus Rhythm Using Ventricular Waveform Morphology", *IEEE Transactions on Biomedical Engineering,* vol. 38, No. 6, (Jun. 1991),561-570.

White, Harley, "Similarity Recovery Post Shock", *U.S. Appl. No. 10/206,978,* (Jul. 26, 2002),42 pgs.

* cited by examiner $$d_k^{j-1} = \frac{c_{2k+1}^j - c_{2k}^j}{\sqrt{2}} \qquad C_k^{j-1} = \frac{c_{2k}^j + c_{2k+1}^j}{\sqrt{2}}$$

DISTINGUISHING SINUS TACHYCARDIA FROM ATRIAL FIBRILLATION AND ATRIAL FLUTTER THROUGH ANALYSIS OF ATRIAL CHANNEL WAVELET TRANSFORMS

STATEMENT REGARDING FEDERALLY SPONSORED RESEARCH OR DEVELOPMENT

This invention was made with U.S. Government support under National Science Foundation award number 9631347. Under this grant, the U.S. Government has certain rights pursuant to the conditions of the grant.

FIELD OF THE INVENTION

The present invention relates generally to the field of implantable cardiovascular defibrillators (ICDs) and more particularly to dual chamber ICDs that utilize dual chamber algorithms to determine when to implement what type of therapy. More particularly, the present invention relates to ways in which such a device may distinguish sinus tachycardia (ST) from non-ST atrial waveforms, for example, atrial fibrillation or flutter.

BACKGROUND AND STATE OF THE ART

Dual chamber ICDs have both atrial and ventricular leads and may thereby monitor the cardiac rhythms that occur in the atria and ventricles separately and independently. As is explained in Chapter 17 of "Nonpharmacological Therapy of Arrhythmias for the $21^{st}$ Century" by I. Singer, S. S. Barold, and A. J. Camm (editors), (Futura Publishing Co., Inc., Armonk, N.Y. 1998), these devices enable P waves, originating in the atria, and R waves, originating in the ventricles, to be independently monitored, such that the P to P and R to R time intervals can be separately monitored, and such that the relative phase relationship of the P-waves and R-waves may also be monitored closely and studied, harmful patterns recognized and identified, and appropriate shock or pacing treatments administered automatically.

Fairly sophisticated techniques have been adopted, in the case of ventricular waveform monitoring, to distinguish ventricular tachycardia (VT) and ventricular fibrillation (VF) from less harmful conditions, such as atrial fibrillation, atrial flutter, and rapid, but not necessarily life threatening, sinus tachycardia (ST). One difficulty with this type of equipment is distinguishing these conditions from each other. The following articles discuss various approaches to improving the performance of ICDs in this area: "Intracardiac Electrogram transformation" by Milton M. Morris, Janice M. Jenkins, and Lorenzo A. DiCarlo, Journal of Electrocardiology, Vol. 29 Supplement, pages 124 to 129 (1996). "Discrimination of ventricular tachycardia from sinus tachycardia by antitachycardia devices: value of median filtering" by Chih-ming James Chiang, Janice M. Jenkins, and Lorenzo A. DiCarlo, Medical Engineering Physics, Vol. 16, pages 513–517 (1994). "A comparison of four New Time-domain Techniques for discriminating Monomorphic Ventricular Tachycardia from Sinus Rhythm Using Ventricular Waveform Morphology" by Robert D. Throne, Janice M. Jenkins, and Lorenzo A. DiCarlo, IEEE Transactions on Biomedical Engineering, Vol. 38, pages 561–570 (IEEE No. 6, June 1991). These articles describe various ways in which the morphology of the ventricular wave can be examined, changes studied, and such things as the degree of change from a normal pattern, as well as the rapidity at which such changes occur, can be determined.

The Chiang et al. article focuses upon changes in the heartbeat interval, where the median (as opposed to the average) of a sequence of five heartbeat intervals is measured and examined for signs of a sudden change, which can signal VT as opposed to ST.

The Throne et al. article teaches the use of correlation waveform analysis (CWA). In this procedure, a "template" waveform, one representing a normal heart rhythm, is correlated against the waveforms actually detected. While this article says that CWA can reliably distinguish between normal and abnormal rhythms, CWA is highly computationally intensive, requiring many multiplications. With battery-powered ICDs, this excess of computations can drain the unit's battery too rapidly. The article explains this problem and explores a number of mathematical algorithms that are less computationally intensive but that give results approaching those achievable with CWA. Templates of the type described in this article also tend to be specific to an individual, and cannot be shared with others.

The Morris, et al. article explores how mathematical transformations, and in particular the Karhunen-Loeve transformation, can be used together with CWA to measure the amplitude of selected morphological features and, by focusing upon transformed values that are associated with particular features, to reduce the number of computations that need to be performed by the CWA between a template and an actual waveform. The transformation reduces the number of coordinate values that need to be correlated and examined. But the Karhunen-Loeve transformation itself is fairly computationally intensive and does not lend itself readily to computational shortcuts such as those utilized, for example, in the fast Fourier transform.

Medtronics, Inc. sells an ICD that uses the Haar wavelet transformation to perform CWA against a template. The Haar transforms are used in this ICD to distinguish ventricular tachycardia (VT) from super ventricular tachycardia (SVT) events, such as atrial fibrillation or flutter or rapid rate sinus tachycardia.

With an atrial lead present, it is also now feasible to study the atrial waveforms more closely. An object of the present invention is to analyze signals received from a bipolar atrial lead to analyze the waveform morphology using the minimum possible number of calculations to conserve battery power and yet reliably to distinguish between atrial ST and non-ST conditions, while also enabling the same apparatus to be used with many different individuals.

BRIEF SUMMARY OF THE INVENTION

Briefly summarized, a first embodiment of the invention may be characterized as an implantable defibrillator or other heart monitoring device designed to distinguish two differing heart rhythms. It includes electrodes that may be attached to the heart of the recipient of the defibrillator or the patient whose heart is being monitored. These electrodes provide electrical representations of heartbeats to a first electronic mechanism that transforms these electrical representations into digital data and performs mathematical computations including at least a partial discrete wavelet transformation upon the digital data, thereby generating at least a subset of discrete wavelet transformation components chosen such that the components generated and retained include components demonstrated to be suitable for use in distinguishing the two differing heart rhythms and also demonstrated to be relatively low in variability from one recipient or patient to another. It further includes a template containing at least a corresponding subset of discrete wavelet transformation components captured from at least one individual whose heart was beating in accordance with one of the two differing heart rhythms when the electrical representations of heartbeats that gave rise to these components were captured and computed generally as described above. In addition, it includes a second electronic mechanism for correlating the subset of transformation components provided by the first mechanism against the subset of transformation components provided by the template, giving rise to a correlation value. And finally, it includes a third electronic mechanism for mathematically examining a time series of the correlation values received from the second mechanism and for giving an indication of whether the first or second of the heart rhythms is present, generally disregarding isolated instances of heartbeat irregularities and focusing upon longer-term trends in the variation of the heart rhythm.

Another embodiment of the invention may be characterized as a method for distinguishing two differing heart rhythms. This method begins by capturing electrical representations of a series of sequential heartbeats. It transforms these electrical representations into digital data and then performs mathematical computations including at least a partial discrete wavelet transformation upon the digital data, thereby generating at least a subset of discrete wavelet transformation components corresponding to at least some of the sequential heartbeats chosen such that the components generated and retained include components demonstrated to be suitable for use in distinguishing the two differing heart rhythms and also demonstrated to be relatively low in variability from one heart to another. It provides a corresponding subset of reference discrete wavelet transformation components that are captured from at least one heart beating in accordance with one of the two differing heart rhythms when the electrical representations of heartbeats that gave rise to these components were captured and computed generally as described above. It correlates each subset of transformation components generated as described in the performing step (above) against the subset of transformation components provided as described in the providing step (above), giving rise to a sequence of correlation values. It repeatedly mathematically examines a time sequence of the correlation values to give an indication of whether the first or second of the heart rhythms is present, generally disregarding isolated instances of heartbeat irregularities and focusing upon longer-term trends in the variation of the heart rhythm as indicated by the correlation values.

Yet another embodiment of the invention may be characterized as an implantable defibrillator or other heart monitoring device designed to distinguish two differing heart rhythms. This device includes electrodes that may be attached to the heart of the recipient of the defibrillator or the patient whose heart is being monitored. It also includes a first electronic mechanism designed to accept electrical representations of individual heartbeat waveforms from the electrodes, transform these electrical representations into digital data, and then perform plural digital filtering operations each focusing upon varying width and varying-positioned windowed portions of each heartbeat waveform to generate a plurality of components, one from each such digital filtering operation, each such component representative of different features of each heartbeat waveform some of which features are spread over the entire width of the waveform and other of which features are concentrated in the varying-width and varying-positioned windowed portions of each waveform, the filtering operations being selected such that the components generated and retained are components determined to be suitable for use in distinguishing the two differing heart rhythms and also determined to be relatively low in the variability of their differing heart rhythm distinguishing capabilities from one recipient or patient to another. It includes a template containing at least a corresponding subset of components generated as described above from heartbeat waveforms captured from at least one individual whose heart was beating in accordance with one of the two differing heart rhythms when the electrical representations of heartbeats that gave rise to these template components were captured. It further includes a second electronic mechanism for correlating the subset of components provided by the first mechanism against the subset of components provided by the template, giving rise to a correlation value. And it includes a third electronic mechanism for mathematically examining a time series of the correlation values received from the second mechanism and for giving an indication of whether the first or second of the heart rhythm is present, generally disregarding isolated instances of heartbeat irregularities and focusing upon longer-term trends in the variation of the heart rhythm.

Further objects and advantages of the invention are apparent in the drawings and in the detailed description that follows. The features of novelty that characterize the present invention are pointed out with particularity in the claims annexed to and forming a part of this specification.

BRIEF DESCRIPTION OF THE DRAWINGS

For a better understanding of the invention, reference will be made to the drawings, wherein.

DETAILED DESCRIPTION OF THE INVENTION

The present invention is directed towards improving the quality and functionality of both implantable cardioverter defibrillators (ICDs) and implantable atrial defibrillators (IADs). All such devices need to have a method and mechanism for accurately distinguishing sinus tachycardia (ST) form non-ST, such as atrial fibrillation and atrial flutter. This method and mechanism should be conservative, biased towards not initiating therapy unless non-ST is clearly indicated. It should also require as few machine computational cycles as possible to reduce ICD and IAD battery drain.

The principle underlying the present invention is that ST and non-ST can be distinguished by studying and measuring the atrial electrogram morphology to detect aberrant conduction in the atria. Thus, by comparing normal ST waveforms to a series of newly-occurring waveforms, ST is indicated by abnormal atrial waveform morphology which signals aberrant conduction within the atria—improper electrical patterns of depolarization. This will show up in the signal potentials captured by a bipolar atrial lead.

Figure 1:
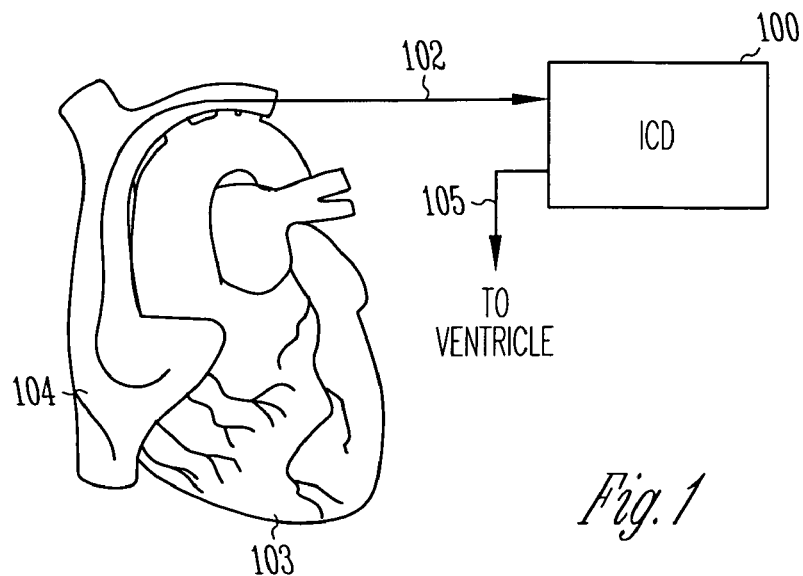
FIG. 1 is an elevational view of a heart illustrating an atrial bipolar lead inserted into the atria region to sense electrical potentials on the surface of the atrial muscles and connecting to an implantable cardiac defibrillator.

With reference to FIG. 1, the present invention can be implemented in an ICD 100 (which could be an IAD) that is implanted in the chest of a patient who suffers from unpleasant and possibly life-threatening irregularities in heart operation due to improper electrical stimulation of the heart muscle cells. During normal heart action, the heart's electrical impulses originate in the sino-atrial node as an action potential that is transmitted smoothly to all portions of the atria, causing contraction of the atrial chambers. The electrical impulse continues in its path to a cluster of conduction fibrils known as the atrioventricular node. After a delay of about one-tenth of a second, an action potential flows over the ventricles and causes them to contract in synchronism with and following shortly after the atrial contraction. In this manner, the heart pumps blood to the lungs and from the lungs to the body.

A bipolar lead 102 is implanted within the atria 104 of a heart 103 to measure the electrical potential between nearby cells of the atria. As the action potential actively passes from cell to cell past the two electrodes of the lead 102, an oscillating signal potential is developed across the two electrodes and is conveyed by the bipolar lead 102 to the ICD 100 where the signal is sampled about 1000 times per second and is digitized, with the sequential samples stored within a RAM memory within the ICD 100 for further analysis. Another bipolar lead 105 may extend to the ventricle (not shown) of the heart 103 to measure the action potentials generated within the ventricles. These same leads, or other leads, may be used by the ICD for administering various types of therapy, such as pacing or defibrillation shock therapy.

The data samples collected from within the atria are now analyzed. First, with reference to data gathered from the ventricles, if some event in the ventricle, such as a mis-timed depolarization event that partially overlaps the atria's P wave, could leak across to the atria and distort the measurement of the potentials for a given atrial depolarization, then the data for that particular heartbeat is discarded and is not used in further analyses. Such distortion can also be found simply because a given heartbeat set of data gathered from the atria is itself badly distorted, and this approach must be taken in the case of an IAD having no ventricular lead. The remaining data is retained for further processing.

In preparation for further processing, the data for individual heartbeats is identified and gathered. The position within the gathered data of the negative spike to the atrial P depolarization waveform is determined and is selected as the center of the waveform for each beat. Then, since data close to this P-wave is to be analyzed, and since data further away may be distorted to some degree by ventricular activity or by variations in the P-to-P interval, 32 sequential data samples are selected for each heartbeat such that the negative spike of the P-wave becomes signal potential sample number 16 of the 32 sequential samples selected for further analyses. These samples for a normal heartbeat appear at 302 in FIG. 3 and at 502 in FIG. 5, where the amplitude of the atrial signal potential is plotted against time over the 32 sampled values, with the negative P-wave spike positioned as signal sample number 16. Likewise, the samples for an abnormal heartbeat appear at 504 in FIG. 5.

Straightforward correlation (CWA) of the 32 samples against a template containing a typical or normal pattern could be performed at this juncture, as taught on page 563 (equation (1)) of the article by Thorne, cited in the introductory portion of this specification. But the performance of such a cross correlation at repeated regular intervals would generate numerous computations and would drain the ICD's battery more rapidly than is desirable. In addition, provision would have to be made for a full template waveform that can be stored within the ICD to be used as a comparison reference. In addition, such templates generally need to be patient specific, and they are more susceptible to normal changes in shape.

Accordingly, to reduce the mathematical complexity of the cross correlation computations, it is desirable to reduce the number of data points from 32 down to some much lower number through the use of some form of transformation into a different set of values. For example, the data could be transformed using the Karhunen-Loeve transformation described in the Morris article cited at the beginning of this specification. But that transformation is fairly computationally intensive. Computationally, a fast Fourier transformation would be more efficient, but any such transformation into the frequency domain, where variable frequency sine and cosine wave amplitudes result from the transformation, does not match itself well to the morphology of atrial heart waveforms, which tend to be formed from large, ringing, spike-like representations of P-wave depolarization events travelling as moving action potential fronts past the pair of electrodes attached to the bipolar lead, and not as steady harmonics extending across time. Accordingly, Fourier-class transforms do not adequately reduce the number of significant data values that must be considered. And in addition, when the "window" size for a Fourier analysis is selected, if it is wide, then the frequency values are not time-specific, but represent average signal harmonic content over the entire window time duration. And if the window is narrow, then the harmonics are too spread out in frequency, and the frequency-domain data generated by the transform does not resolve things finely enough in the frequency domain.

For all of the above reasons, the present invention analyzes the waveforms using a discrete wavelet transform. This has the advantage that while low frequency wavelets are broad in time, high frequency wavelets have a much narrower timeslot focus. Thus, for example, with 32 data samples taken sequentially over time, a wavelet transformation generates a D.C. wavelet that spans the entire set of 32 points; a first reversing wavelet that also spans the entire set of points; two second harmonic wavelets that each focus upon only one-half of the 32 data points; four third harmonic wavelets that each focus upon only one-fourth of the 32 data points; eight fourth harmonic wavelets that each focus upon four of the 32 data points; and 16 fifth harmonic wavelets that each focuses upon only two of the 32 data points. Accordingly, the higher-frequency wavelet amplitudes are quite time specific, unlike Fourier sinusoidal amplitudes, while the lower-frequency and D.C. wavelet amplitudes give one broad information about the whole set of 32 points. And like the Fourier transform, the discrete wavelet transform preserves all of the information of the original atrial signal, such that the transformation is fully reversible. 32 discrete wavelet transform values may be reverse transformed back into 32 values indicating the atrial signal potentials at 32 sequential points in time.

In essence, the Haar function is performing multiple digital filtering operations, at variable positions and utilizing varying-width windowing functions, to develop component values that represent varying types of heartbeat activity, at varying frequencies, spread over varying widths, and located at varying positions. These component values can be studied to see which subset of these component values are good at distinguishing ST from non-ST, or (more generally) which subset of these component values are good at distinguishing one type of heartbeat waveform from another. Further study of such a selected subset can further determine which of the subset of components are relatively invariant from one individual's heart to another. One preferably selects component values that are suitable from both of these two perspectives.

The particular wavelet transformation to choose can be tailored to the nature of the data, with the wavelets chosen to resemble somewhat the values to be found within the data so that some transformed values are of much larger amplitude than others, and such that the low amplitude transformed values may be disregarded. Of particular importance with an atrial P waveform of the type being analyzed here are wavelets having frequency values roughly comparable to and timed to coincide with the ringing of the atrial depolarization. This tailoring can minimize the number of transformed data values that are significant and that are candidates for full participation in the correlation analyses to determine if there has been a substantial change in waveform morphology.

Another factor in selecting a particular wavelet transformation is reducing the number of computations that must be performed to carry out the transformation. Yet another factor is selecting a wavelet transformation where some of the transformed component values vary from normal to abnormal heart rhythms in much the same over a population of individuals so that a generic template of these component values may be derived that can be used with many individuals, rather than with just one individual.

Figure 3:
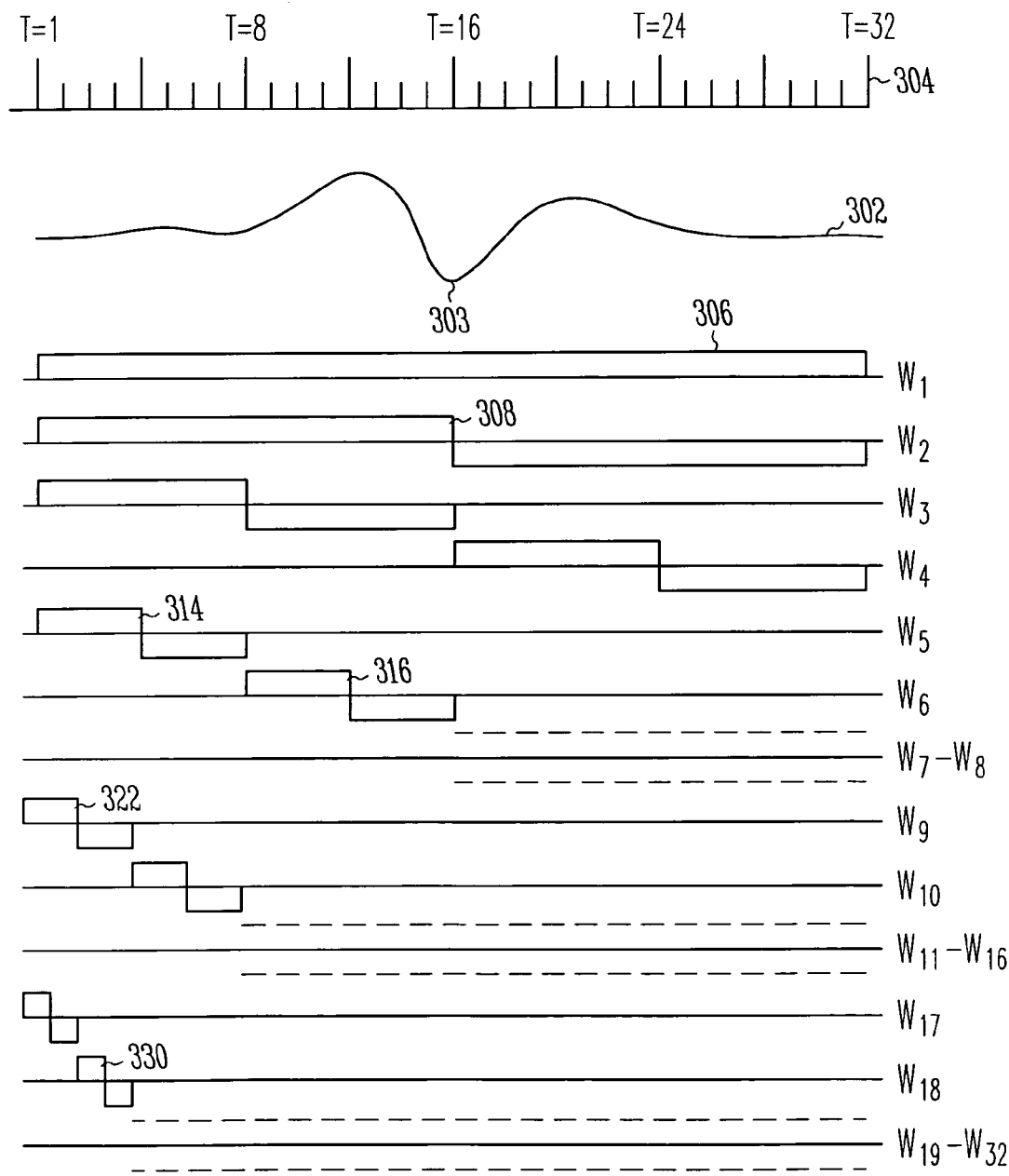
FIG. 3 shows a timing diagram in which a typical normal atrial waveform, with its negative peak centered at the $16^{th}$ time sampling position, is shown next to a scale illustrating the positions of 32 sampling points in time, and also next to a chart containing representations of all the Haar transformation wavelets $W_1$ through $W_{32}$.

These factors suggest that the Haar transformation would be a suitable candidate for use in analysis of atrial waveforms and possibly other waveforms as well. With reference to FIG. 3, in the case of 32 voltage values sampled over time, the 32 applicable Haar discrete transform wavelets appear as shown in this figure. Other discrete wavelet transforms based upon wavelets having triangular or other shapes may also prove usable. The Haar transform wavelets, in particular, have the shape of a square waveform, as will be described, and this can simplify the computations required.

In FIG. 3, time increases from left to right. A scale 304 indicates the 32 points in time at which the atrial waveform is sampled, and an analog atrial waveform (before digitization) is shown at 302. The P wave negative notch 303 is shown centered at the $16^{th}$ timeslot so that the signal potential of the atria waveform sampled at this point in time becomes the $16^{th}$ data value in the set of 32 data values that are to be subjected to the Haar transformation.

A Haar wavelet is simply one cycle of a square waveform that starts at zero, then swings positive (to "+1"), then swings negative (to "−1"), and then swings back to zero. The wavelet $W_2$, shown at 308 in FIG. 3, for example, is at "+1" at points in time 1 to 16 and is at "−1" at points in time 17 to 32. The shorter waveform $W_6$, shown at 316 in FIG. 3, is at "+1" at points in time 9 to 12 and is at "−1" at points in time 13 to 16, and is at "0" at all other points in time. The waveform $W_1$, shown at 306 in FIG. 3, is so slow to fluctuate in time that its "−1" portion is off of the chart (in FIG. 3) to the right, and is ignored; and accordingly, it has the value "+1" for all 32 of the points in time shown in FIG. 3. It thus represents the average, or D.C., component of the atrial signal potential.

The lowest frequency wavelets $W_1$ and $W_2$ encompass the entire set of 32 points in time. The higher frequency wavelets $W_3$ and $W_4$ each encompasses only half of the points in time, and the two wavelets taken together encompass all the points in time. The four wavelets $W_5$, $W_6$, $W_7$, and $W_8$ each encompasses only eight points in time, and the four wavelets taken together encompass all points in time. The eight wavelets $W_9 \ldots W_{16}$ each encompasses only four points in time, and together all eight wavelets encompass all points in time. And finally, the wavelets $W_{17} \ldots W_{32}$ each encompass only two points in time, but the sixteen wavelets together encompass all points in time. Thus, each wavelet has a characteristic time span and position as well as a characteristic frequency, with higher-frequency wavelets having a narrower and more specific time span and position than lower-frequency wavelets. This is advantageous with an impulse-type, ringing signal such as the atrial depolarization waveform considered here, since many higher-frequency transform values that correspond to Haar wavelets positioned in time away from the P waveform or that do not correspond to its frequency of ringing may be low in amplitude such that they may safely be ignored during the analysis steps, thereby reducing the data that must be processed during the correlation steps.

(The above, while presented in the context of the Haar wavelet, is also applicable to other wavelet shapes that may used to perform a discrete wavelet transform (DWT)).

Each of the 32 Haar transformed values is computed as follows: Multiply each of the 32 sampled and digitized voltage values representing the analog atrial waveform 302 by the correspondingly-positioned-(in-time) amplitude values of one of the 32 Haar wavelets (shown in FIG. 3); then sum the resulting products; and then multiply the resulting sums by a discrete wavelet transform scaling factor $2^{-j/2}$, where j equals 1 for the wavelets $W_{17}$ to $W_{32}$, 2 for $W_9$ to $W_{16}$, 3 for $W_5$ to $W_8$, 4 for $W_3$ to $W_4$, and 5 for $W_1$ and $W_2$. For example, and referring to FIG. 3: the first wavelet $W_1$ is always +1, so the atrial signal potential values are simply summed and then multiplied by $2^{-5/2}$; the second wavelet is +1 for time points 1 to 16 and −1 for time points 17 to 32, so the first 16 values are summed, the second 16 values are summed, the difference between the first and second sums is computed, and the result is multiplied by $2^{-5/2}$; and so on until all the transformed values have been computed, one for each Haar wavelet. The 32 time-sequential atrial signal potential values are thus transformed into 32 Haar wavelet amplitude values which may be called "transformed values" and which may be assigned the numbers 1 to 32 corresponding to the subscript numbers of the Haar wavelets to which they each correspond and whose amplitudes they represent.

The above description of how to compute the Haar wavelet transformed values is accurate, but it is not the most efficient way to proceed in the case of Haar wavelets. Like the Fourier transform, which has a corresponding fast Fourier transform that saves intermediate results and thereby avoids re-computing them and thus reduces substantially the number of computations, the Haar transformation also may be carried out in a manner that saves intermediate sums and re-uses them to reduce substantially the number of computations. This is described below at the point where FIG. 4 is described, since FIG. 4 illustrates graphically how this can be done. The illustrative program listing presented below is also an implementation of the fast Haar wavelet transformation algorithm.

The Haar transformation can readily be carried out by any digital computer. As an example of how the Haar transformation can be carried out on 32 values, the following program, written in the language C, is illustrative of many possible programs that may be written.

In the exemplary program that follows, a 32-element array YY contains 32 data values representing the 32 sampled atrial signal potential values representing the fluctuations over time of the signal supplied by the bipolar lead 102. The analog atrial signal is sampled, digitized, broken into separate beat data sets, pre-processed (to remove waveforms distorted by ventricular activity), centered (with the negative depolarization spike at data point 16), and fed into the subroutine presented below. This subroutine is compiled (or assembled, if rewritten in assembly language) and installed in the ROM of the ICD's embedded microprocessor. This subroutine returns, contained within the same array YY, the 32 transformed Haar wavelet amplitude values described above. (The constant value "RecipSqrtTwo" is the reciprocal of the square root of two). An illustrative version of the subroutine for computing all 32 of the Haar transformed values in an efficient manner is presented here:

```
void Haar (double yy[])
{
    int I, j, L;
    double zz[32];
    for(I = 5; I > 0; I--)
    {
        L = 1;
        for (j = 1; j <= I; ++j) L = 2 * L;
        for (j = 0; j < L; ++j) zz[j] = yy[j];
        for (j = 0; j < L - 1; j = j + 2)
        {
            yy[j/2] = RecipSqrtTwo * (zz[j] + zz[j + 1]);
            yy[(j + L)/2] = RcipSqrtTwo * (zz[j] - zz[j + 1]);
        }
    }
    return;
}
```

The above program computes the 32 Haar transformed values 1 to 32 from the 32 atrial signal potential time-sequenced input values. It does so with only 31 additions, 31 subtractions, and 62 multiplications. It is carefully designed to compute each value in a systematic way, making multiple use of intermediate results.

First, the program computes sixteen sums of and sixteen differences between eight adjacent pairs of the 16 time sequenced atrial signal potential values, and the sixteen difference values become the Haar transformed values 17 to 32, reflecting the strength of the highest frequency Haar wavelets positioned at 16 different positions in time, corresponding to the wavelets $W_{17}$ to $W_{32}$ shown in FIG. 3. All the sum and difference values are scaled by multiplication by $2^{-1/2}$. Next, taking the 16 sums of atrial signal potential values as an intermediate result, the above algorithm generates eight sums of and eight differences between adjacent pairs of these sixteen intermediate values that resulted from the first sixteen additions, and the eight newly-computed difference values become the Haar transformed values 9 to 16, reflecting the strength of the second to the highest frequency values at eight different points in time, corresponding to wavelets $W_9$ to $W_{16}$ in FIG. 3. All of these eight sum and eight difference values are again scaled by $2^{-1/2}$ so that the wavelets $W_9$ to $W_{16}$ are scaled by ½ ($2^{-2/2}$ or $2^{-1/2}$ times $2^{-1/2}$). Next, taking these eight sums of sums of adjacent atrial signal potential values as an intermediate result, the above algorithm generates four sum and four difference values, again scaling by $2^{-1/2}$, and the four difference values become Haar transformed values 5 to 8, reflecting the strength of the middle frequency wavelets at four different points in time, and corresponding to wavelets $W_5$ to $W_8$ in FIG. 3. Next, taking these four sums of sums of sums of adjacent atrial signal potential values, the above algorithm generates two sum and two difference values, again scaling by $2^{-1/2}$, and the two difference values become Haar transformed values 3 and 4, reflecting the strength of the second to the lowest frequency wavelets only two of which encompass all the time domain data, corresponding to the wavelets $W_3$ and $W_4$ shown in FIG. 3. And finally, the algorithm generates the sum of and the difference between the final remaining two sums of sums of sums of sums of atrial signal potential values, again scaling by $2^{-1/2}$. The difference value is then the Haar transformed value 2, representing the strength of the lowest-frequency wavelet, the one corresponding to the wavelet $W_2$ in FIG. 3, the wavelet that extends the full length of the time scale. The sum value is then the first, or D.C., transformed value, representing the average signal potential level over the 32 sampled points in time, which corresponds to the wavelet $W_1$ in FIG. 3.

Figures 4A, 4B:
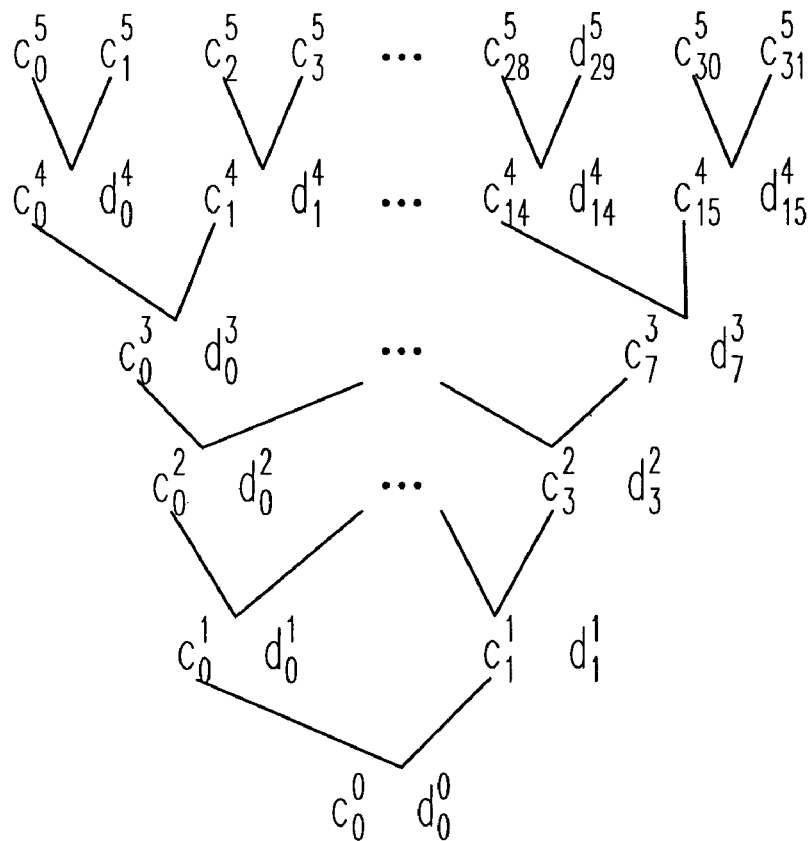
FIGS. 4A and 4B illustrate the manner in which 32 digitized samples of the atrial signal 302 in FIG. 3 can be mathematically processed and converted into 32 Haar transformed values.

Another way of viewing this computation is illustrated in FIGS. 4A and 4B. The 32 atrial signal potential values are shown at the top of FIG. 4A and are identified as $c_0^5$ through $c_{31}^5$. The superscript "5" indicates that these values are processed when the index value "N" in the above computer program is equal to "5"—that is, during the first pass through the data generating intermediary sums and differences. During subsequent passes, the value of N is decremented to 4, 3, 2, and finally to 1. During each pass through the data, the computer generates sums $c^{N-1}$ and differences $d^{N-1}$, as shown in FIG. 4B, between adjacent pairs of the values $c_0^N$ and $c_1^N$; $c_2^N$ and $c_3^N$; and so on, so that the number of newly-generated $c^{N-1}$ and $d^{N-1}$ terms is reduced by half with each computer pass through the intermediary results. At the end of all these computations, the value $c_0^0$ is the first, or D.C., Haar transformed value; and the values $d_0^0$; $d_0^1$ and $d_1^1$; $d_0^2$, $d_1^2$, $d_2^2$, and $d_3^2$; $d_03$, $d_1^3$, ... and $d_7^3$; and $d_0^4$, $d_1^4$, and $d_{15}^4$ are, respectively, the remaining Haar transform values 2 through 32. FIG. 4 thus illustrates quite succinctly how all the transform computations are carried out, and how the intermediary "c" sum values, such as $c_0^4$, are used to compute multiple Haar values, such as the values $d_0^3$, $d_0^2$, $d_0^1$, $d_0^0$, and $c_0^0$ all of which are computed from the intermediary value $c_0^4$. Saving and reusing these intermediary "c" values saves much computational time. FIG. 4B indicates the precise addition and subtraction operations that are carried out at each level to compute the values in the next lower level, proceeding down through the chart presented in FIG. 4A.

But in any given application to heart waveform analysis, all of these computations may not be needed, and accordingly the number of computations may be reduced much further. Since the present invention teaches that only a small number of these Haar transformed values need actually be considered, a far less computationally intensive transform can be developed which only generates the intermediate and final transformed values that are actually needed to generate the specific Haar transformed values which have proved to be significant in discriminating between sinus tachycardia (or ST) and non-ST conditions. All others need not be computed, and the above program may be reduced to a special algorithm that omits as many sums, differences, and multiplications as possible.

For example, if only the transformed values 1, 5, 9, and 24 are significant, then 31 additions are required to compute the first transformed value (the D.C. value—the simple sum of all the time domain signal values); six additions and one subtraction are required to compute the fifth transformed value (in FIG. 3, the difference between the sums of time domain values under each half of the wavelet $W_5$ at 314 in FIG. 3); two additions and one subtraction are required to compute the ninth transformed value (in FIG. 3, the difference between the sums of the time domain values under each half of the wavelet W9 at 322 in FIG. 3); and only one subtraction is required to compute the $24^{th}$ transformed value (in FIG. 3, the difference between the two time domain values under the respective halves of the wavelet $W_{24}$ (not shown) which is the same size as, but differently positioned in time than, the wavelet $W_{18}$ at 330 (FIG. 3). Accordingly, if only the transformed values 1, 5, 9, and 24 actually evaluated, then only 42 additions and subtractions are required.

But even this number can be reduced further. If the computational algorithm set forth in the above illustrative computer program is followed as a guide, then the intermediary sums used in computing the Haar first, or D.C., transformed value can be re-used to compute the sums for the Haar transformed values 5 and 9, assuming these intermediary results are saved in the manner described in the above program example. Then 31 additions are still required to compute the first transformed value, but only one subtraction is required to compute each of the transformed values 5, 9, and 24, giving a total of additions and subtraction of only 34 operations. And if only transformed values 1, 5, and 9 are computed, the number of additions and subtractions is reduced to 33. And if the first transformed value is omitted and if transformed values 5, 9, and 24 are selected, then the 31 additions needed to compute the first transformed value are not required. Then the number of computations for transformed value 5 is 8 additions and one subtraction; the number of computations for transformed value 9 is 2 additions and one subtraction; and the number of computations for transformed value 24 is still just one subtraction. So the total number of additions and subtractions is just 13. But even this number can be reduced to 11 when it is realized that the two additions done for the transformed value 9 are also done (in the above computational algorithm) when computing the transformed value 5. So the number of additions and subtractions can be reduced to 11.

Also, when computing such a small number of transformed values, the number of multiplications can be reduced as well by postponing the multiplications until a transformed value is actually computed. With reference to FIG. 4A, instead of dividing every sum and difference by the square root of two (as shown in FIG. 4B), several vertical sums of "c" values in different rows of the FIG. 4A table can be formed, and then a "d" value can be computed by subtraction, and then the resulting unscaled transformed value can be scaled with a single multiplication by $2^{-j/2}$ where j is the number of rows in the table of FIG. 4A traversed by the one or more sum and the one difference computations. Thus, the number of scaling multiplications can sometimes be equal to the number of transformed values that are computed, typically 3 or 4.

Accordingly, by using wavelet analysis and transformation, instead of Fourier or discrete cosine or other sinusoid analysis and transformation, a highly useful and highly frequency-specific result can be achieved with a very small number of computations, thereby conserving power and battery life, and yet achieving a high degree of precision in recognizing changes in morphology.

In our tests, we have selected certain transformed values as being much more significant than other values in distinguishing between ST and non-ST. We focused upon those transform values whose "+1" and "−1" scope included the middle 8 time points most significant to analysis of the peak of the atrial depolarization. Working across test data samples obtained from patients who had dual chamber ICDs, we computed the variance of each transformed value for ST and non-ST events using the standard statistical formula for computing variance.

We then calculated the ratio of the variance of non-ST events to the variance of ST events, and selected those terms with the highest variance ratios for further consideration.

In this manner, we reduced the number of transformed values that were included in the CWA or correlation process while always maintaining or improving the performance achieved. Ultimately we settled upon the three or four transformed values having the highest ratios. These were the transform values 1, 5, 9, and 24. We tested 1, 5, and 24 together; 5, 9, and 24 together; and 1, 5, 9, and 24 together. These selected Haar transform values, when used in these combinations, required minimal computations and thereby produced a savings in battery power, and that also gave better performance at distinguishing ST from non-ST than did all of the transformed values used together. So an increase in accuracy was achieved as well as a decrease in computational complexity by this approach to atrial waveform analysis.

Figure 5:
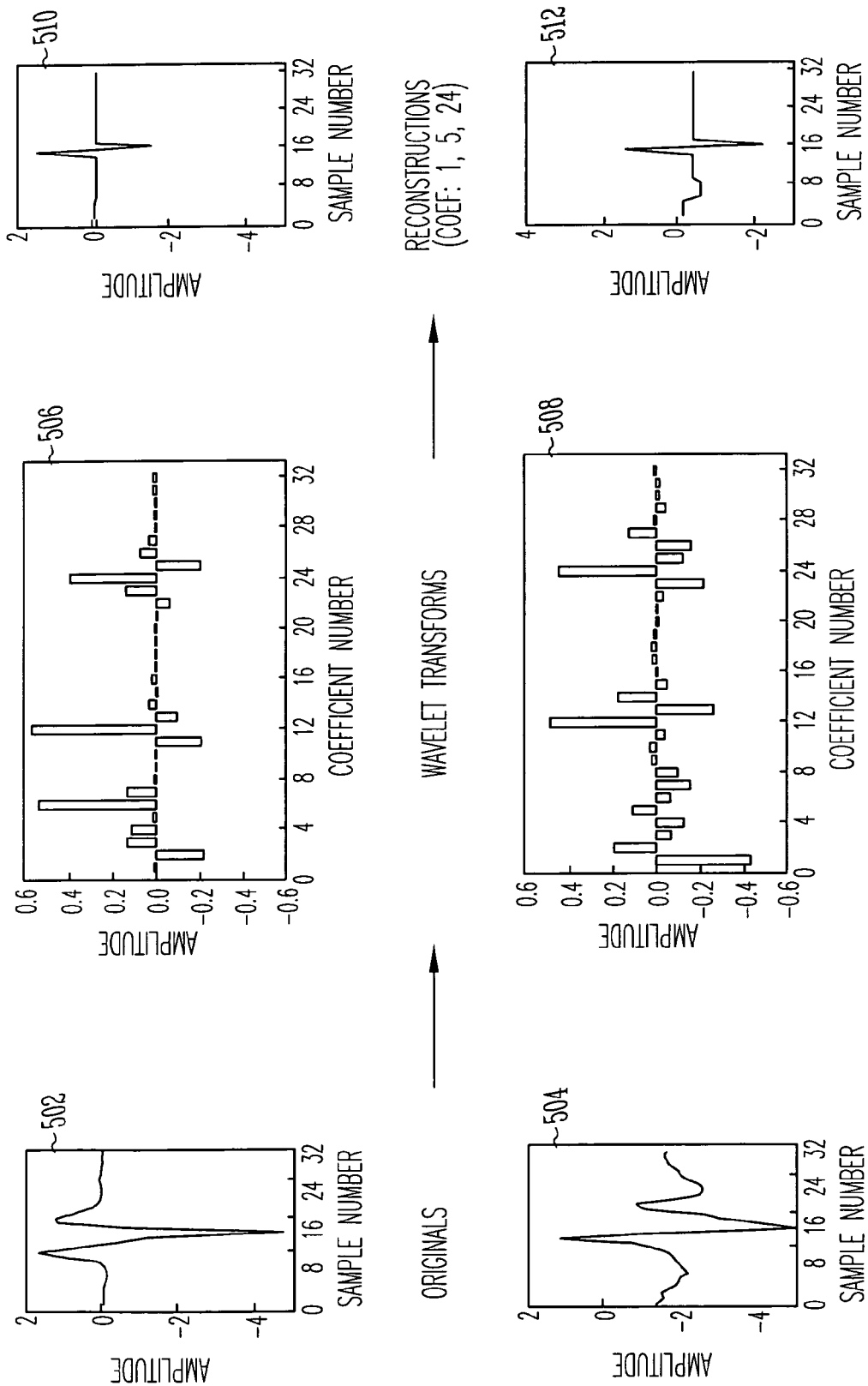
FIG. 5 illustrates, for both normal and abnormal atrial waveforms, with the negative P wave spike positioned at the $16^{th}$ time sampled position, how 32 sequential atrial signal potential samples which comprise these waveforms may be transformed from their normal signal amplitude versus time format into representation by 32 Haar transformed values; and it also illustrates how the reverse transformation of only three of the Haar transformed values back into signal amplitude versus time representation reflects the difference in ST and non-ST.

FIG. 5, for example, illustrates actual plots of digital information illustrating the effect of using only the three coefficients 1, 5, and 24. At 502, a normal waveform is shown, with amplitude plotted against sample numbers from 1 to 32. At 504, an abnormal waveform is shown, again with amplitude plotted against sample numbers. After the Haar transformation, at 506 and 508, the wavelet coefficient amplitude values are indicated for the coefficients 1 to 32. At 506, the coefficients generated by the normal waveform 502 are shown, and at 508, the coefficients generated by the abnormal waveform 504 are shown. One may directly compare these component values and verify that the coefficients 1, 5, and 24 at 506 and at 508 vary significantly in amplitude. Comparison of this same information among different patients (not shown in this figure) also indicated that this variation is relatively constant from one patient to another. At 510 and 512, using only the coefficients 1, 5, and 24, the heartbeat waveforms are reconstructed by a reverse transformation, the normal reconstructed waveform shown at 510 and the abnormal reconstructed waveform shown at 512. The marked differences between these two reconstructed waveforms highlights the way in which these three coefficients can signal an abnormal condition with less computation.

In a practical system, a small number of transform values are selected, in the manner just described. The algorithm for computing these values is then refined, as explained above, to reduce the number of additions, subtractions, and multiplications to the minimum possible while preserving the accuracy of the computations.

We first compute a value $\rho$, which is the correlation between these values with the corresponding values in a template that represents the values for an average normal population.

We then compare this value $\rho$ to a threshold correlation value $\beta$ that is chosen to give optimal results on experimental data. (See the examples in the tables presented below.)

For each waveform analyzed, a test is made to determine whether $\rho$ is greater than $\beta$. If so, then this waveform is placed into the buffer marked "ST" at step 210. If not, then this waveform is placed into the buffer marked "non-ST" at step 211.

Finally, after ten waveforms have been analyzed, a count of ST and non-ST marked waveforms is made to see if the count of non-ST waveforms is greater than some threshold value X (at step 212), where X can be, for example, 7. If more than seven waveforms are non-ST, then therapy is delivered at step 214.

Figure 2:
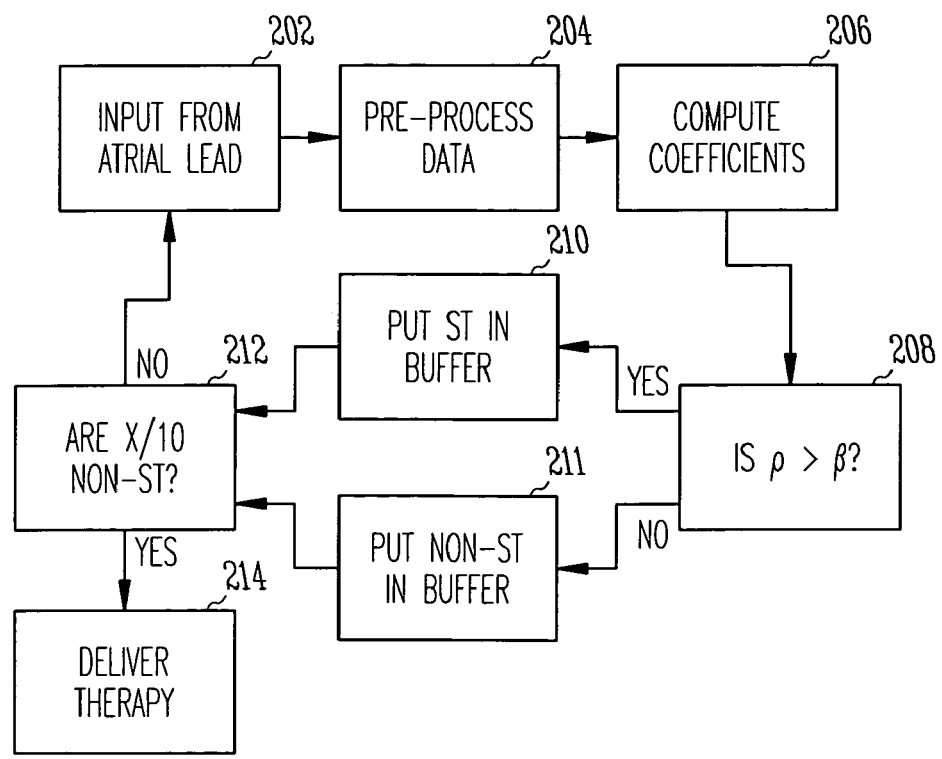
FIG. 2 is a block diagram of the processing steps that are performed upon the data gathered as shown in FIG. 1.

The buffers at steps 210 and 211 in FIG. 2 are buffers that hold the last ten decision values. These buffers can be pictured as sliding windows revealing the most recent ten values to permit the decision at 212 to be continuously updated. The buffers thus function as a nonlinear filter preventing irregular values from delivering therapy improperly. In developing a working prototype of this system, we used a development data set consisting of 20 episodes of ST taken from 4 patients and 18 episodes of AF taken from 7 patients.

| Patient Number | Episodes of ST | Episodes of AF |
| --- | --- | --- |
| 1 | 2 | 6 |
| 2 | 12 | 0 |
| 13 | 0 | 1 |
| 4 | 0 | 2 |
| 5 | 5 | 1 |
| 6 | 0 | 3 |
| 7 | 0 | 3 |
| 8 | 0 | 2 |
| 9 | 1 | 0 |
| TOTAL | 20 | 18 |

We used this data to optimize our choice of $\rho$ and $\beta$ and also the particular coefficients that we chose to examine.

Next, we tested our prototype using a set of 16 episodes of ST obtained from 4 patients together with 17 episodes of AF obtained from 7 patients.

| Patient Number | Episodes of ST | Episodes of AF |
| --- | --- | --- |
| 1 | 8 | 0 |
| 2 | 3 | 1 |
| 3 | 3 | 0 |
| 4 | 2 | 0 |
| 5 | 0 | 4 |
| 6 | 0 | 4 |

-continued

| Patient Number | Episodes of ST | Episodes of AF |
| --- | --- | --- |
| 7 | 0 | 3 |
| 8 | 0 | 3 |
| 9 | 0 | 1 |
| 10 | 0 | 1 |
| TOTAL | 16 | 17 |

We achieved the following performance results using this approach:

| Coefficients | X out of 10 | Threshold ($\beta$) | Sensitivity | Specificity |
| --- | --- | --- | --- | --- |
| 1, 5, 9, & 24 | 3 | 0.808 | 76% | 94% |
| 1, 5, 9, & 24 | 5 | 0.975 | 88% | 94% |
| 1, 5, 9, & 24 | 6 | 0.976 | 82% | 94% |
| 1, 5, 9, & 24 | 7 | 0.983 | 88% | 94% |
| 1, 5, & 24 | 3 | 0.815 | 82% | 94% |
| 1, 5, & 24 | 4 | 0.943 | 88% | 94% |
| 1, 5, & 24 | 5 | 0.956 | 82% | 94% |
| 1, 5, & 24 | 7 | 0.991 | 94% | 94% |
| 5, 9, & 24 | 8 | 0.9993 | 82% | 94% |
| 5, 9, & 24 | 9 | 0.9997 | 76% | 81% |

The quality of the selected subset of transformed values for characterizing changes in morphology may be demonstrated graphically, as indicated in FIG. 5, by performing a reverse Haar transform using only the three or four or so selected transformed values. As can be seen (at 510 and 512 in FIG. 5), the inverse transformations produce distorted representations of the original atrial waveforms which illustrate how the choice of transform values can emphasize the changes. This is another useful way to assist one in selecting which transformed values are most useful.

One feature of the invention is its ability to use a template derived from an average normal population, rather than deriving a patient customized average normal template for each individual patient. Prior systems have required each new patient to be monitored while in a normal state, and the captured data was then averaged to form a patient specific normal template. Contrary to this, the present invention achieved the results shown above using the same template for all patients. Accordingly, the invention may be used with a new patient without the necessity of such preliminary testing of each patient and without a new customized template necessarily having to be created for each patient.

One reason why the present invention can function using a template that represents average values for a normal population is because the specific coefficients selected in the transform domain, in addition to having been selected to emphasize the difference between normal and abnormal values, are also preferably chosen to minimize the differences between different patients. In some cases, values that were good at distinguishing between normal and abnormal rhythms for one patient were not as good at doing so for some other patient. These values are preferably not selected for use in implementing the present invention.

For example, the transform coefficients may be selected such that all (or most of) the normal values of a particular coefficient gathered from many patients had the same sign (positive or negative) and similar amplitudes (or if they varied in sign, they were near to zero). In addition, the abnormal coefficients are significantly different in value from the normal coefficients for each particular patient.

Figure 6:
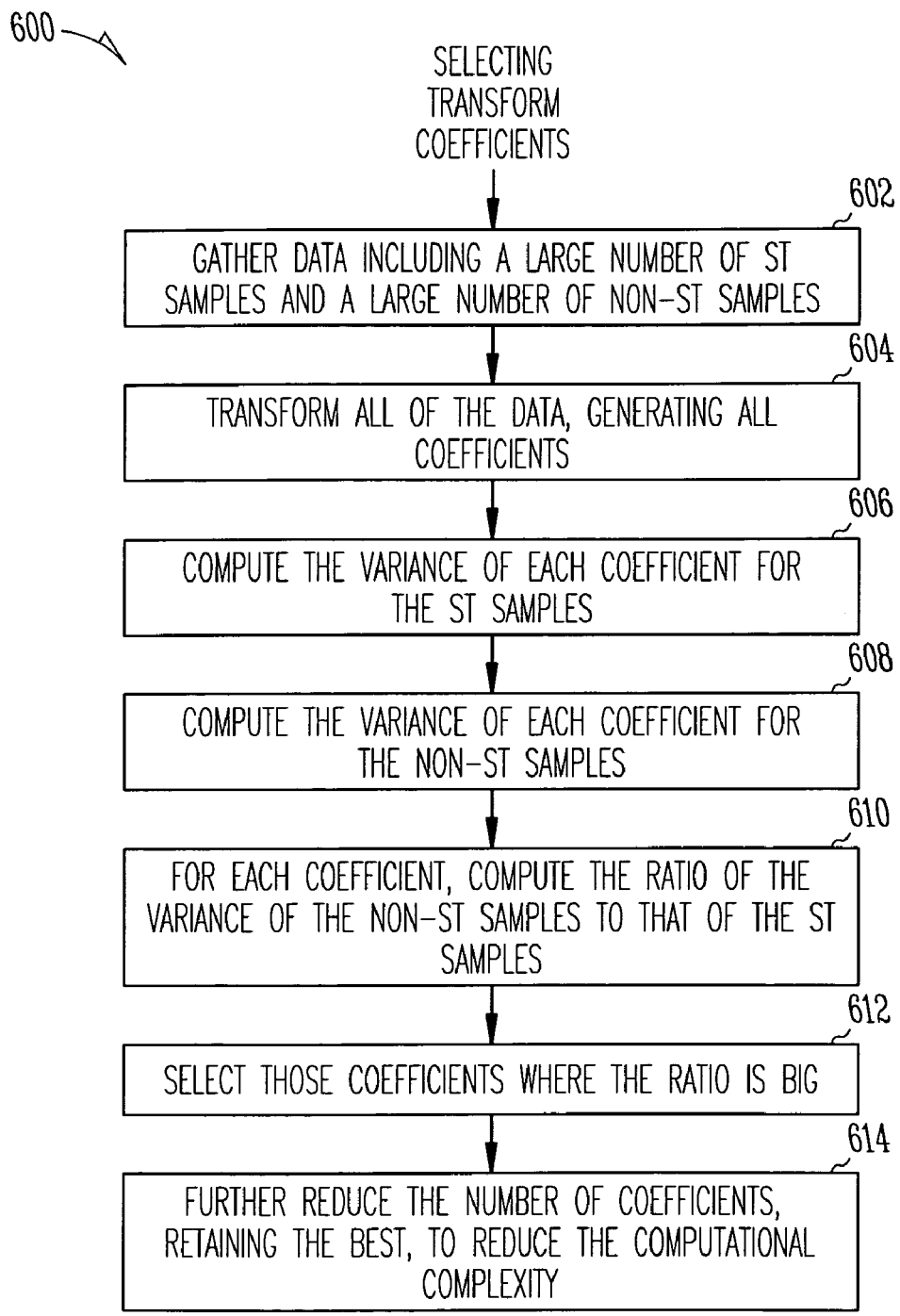
FIG. 6 is a block diagram illustrating the steps involved in selecting the transform coefficients, such as the coefficients 1, 5, and 24 that are used illustratively in FIG. 5.

FIG. 6, at 600, illustrates one way in which this may be done. First, at step 602, one gathers a large number of ST and non-ST data samples. Next, all of this data is transformed, generating coefficients for every waveform set of data (step 604). The variance of each coefficient is then computed first for the ST samples (step 606) and then for the non-ST samples. Then, for each coefficient, the ratio of the variance of the non-ST samples to that of the ST samples is computed (step 608). Finally, those coefficients whose variance ratio was large may be selected a coefficients for use in creating a population template and in testing patients (step 612). In addition, at step 614, the number of coefficients retained may be further reduced to reduce the number of computations that need to be performed, as explained above.

Figure 7:
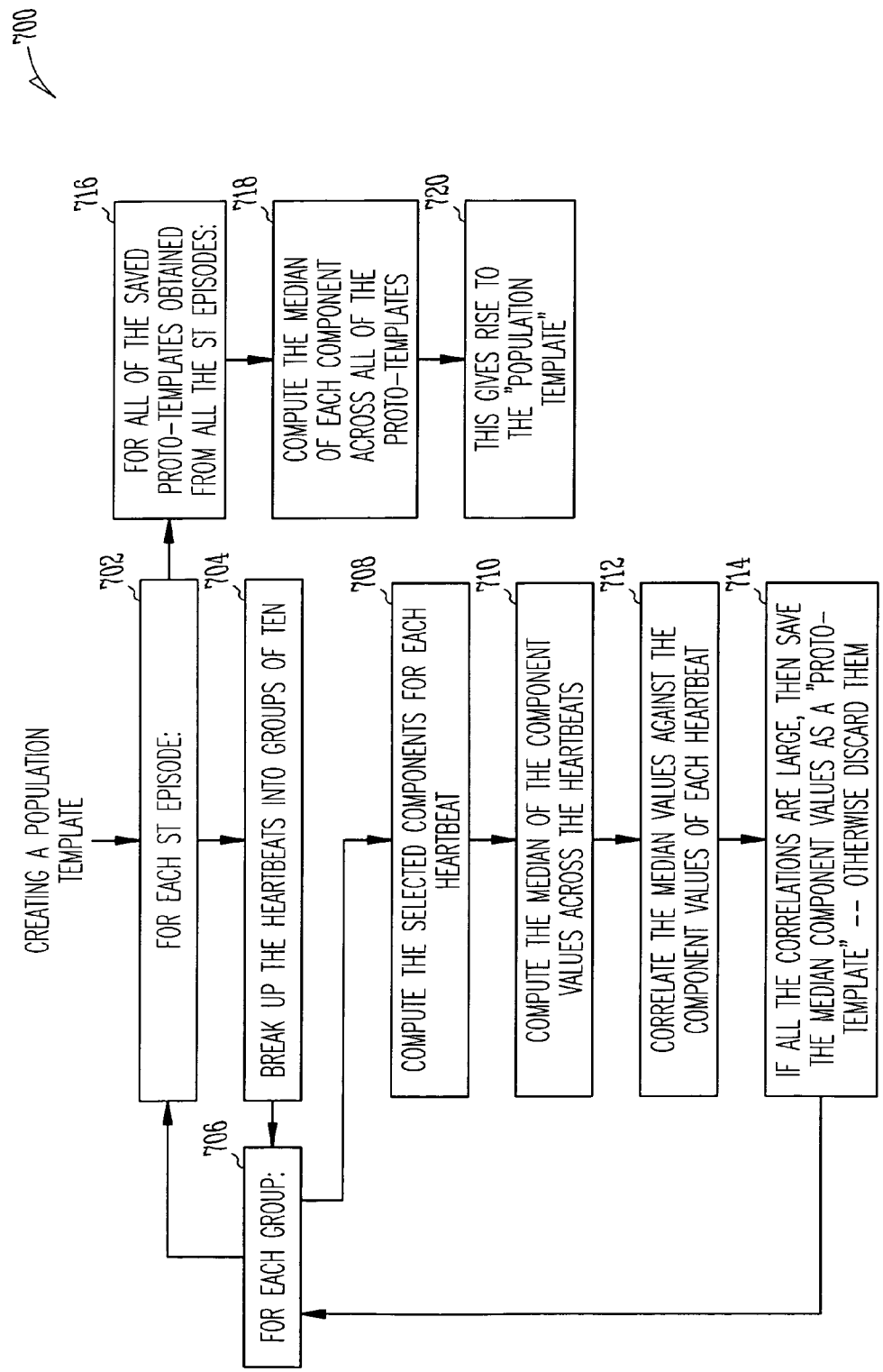
FIG. 7 is a block diagram illustrating the steps involved in creating a population template for use in testing patients.

In the version of the invention that was used to generate the data shown above, the population template was computed as follows, using the 20 ST episodes in the development data set (also used in the first of the two tables presented above). This is illustrated at 700 in FIG. 7.

First, the coefficients were selected as was explained above and as shown in FIG. 6. Next, for each patient episode of ST (step 702), the recorded heartbeats were broken up into groups of ten consecutive heartbeats (step 704). For each group (step 706), the selected coefficients of the Haar transform were computed (step 708) for each of the ten heartbeats and the median value was then selected (step 710) for each coefficient to form a proto-template. If these median values correlated well with the coefficient values for each of the ten heartbeats, the proto-template was retained (step 714). Otherwise, it was discarded.

In this manner, a whole bunch of proto-templates were obtained from each patient episode. Next, median values of the coefficients from all of the proto-templates (step 716) were computed (step 718). These values were then used as the population template for distinguishing ST from non-ST events (step 720).

While the preferred embodiment of the invention has been described above, it is to be understood that numerous modifications and changes will occur to those who are skilled in the art to which the invention pertains. Accordingly, the following claims annexed to and forming a part of this specification are intended to define the true spirit and scope of the invention—that is, what is new and what is desired to be secured by Letters Patent of the United States.

What is claimed is:

1. An implantable defibrillator or other heart monitoring device designed to distinguish two differing heart rhythms comprising:

electrodes that may be attached to the heart of the recipient of the defibrillator or the patient whose heart is being monitored;

a first electronic mechanism designed to accept electrical representations of heartbeats from the electrodes, transform these electrical representations into digital data, and perform mathematical computations including at least a partial discrete wavelet transformation upon the digital data, thereby generating at least a subset of discrete wavelet transformation components chosen such that the components generated and retained include components demonstrated to be suitable for use in distinguishing the two differing heart rhythms and also demonstrated to be relatively low in variability from one recipient or patient to another;

a template containing at least a corresponding subset of discrete wavelet transformation components captured from at least one individual whose heart was beating in accordance with one of the two differing heart rhythms when the electrical representations of heartbeats that gave rise to these components were captured and computed as described above;

a second electronic mechanism for correlating the subset of transformation components provided by the first mechanism against the subset of transformation components provided by the template, giving rise to a correlation value; and a third electronic mechanism for mathematically examining a time series of the correlation values received from the second mechanism and for giving an indication of whether the first or second of the heart rhythms is present, eliminating isolated instances of heartbeat irregularities and focusing upon longer-term trends in the variation of the heart rhythm.

2. A defibrillator or other heart monitoring device in accordance with claim 1 wherein the discrete wavelet transformation is the Haar transformation.

3. A defibrillator or other heart monitoring device in accordance with claim 2 wherein digital samples of the electrical representations of each heartbeat are taken centered about the P wave notch.

4. A defibrillator or other heart monitoring device in accordance with claim 3 wherein, if the digital samples are numbered such that the sample corresponding to the P wave notch is number 16, the subset correlated includes one or more of the transformed Haar coefficients 1, 5, 9, and 24.

5. A defibrillator or other heart monitoring device in accordance with claim 4 wherein the subset correlated includes all of the transformed coefficients 1, 5, 9, and 24.

6. A defibrillator or other heart monitoring device in accordance with claim 4 wherein the subset correlated includes all of the transformed coefficients 1, 5, and 24.

7. A defibrillator or other heart monitoring device in accordance with claim 4 wherein the subset correlated includes all of the transformed coefficients 5, 9, and 24.

8. A defibrillator or other heart monitoring device in accordance with claim 1 wherein at least some of the electrodes are intended to be attached to the atria.

9. A defibrillator or other heart monitoring device in accordance with claim 1 wherein at least some of the electrodes are intended to be attached to the ventricles.

10. A defibrillator or other heart monitoring device in accordance with claim 1 wherein the first electronic mechanism includes a mechanism for detecting and eliminating possibly distorted heartbeat representations from participating in further analysis.

11. A defibrillator or other heart monitoring device in accordance with claim 10 wherein the first electronic mechanism receives atrial data, and the mechanism for detecting and eliminating receives ventricle data and eliminates heartbeat representations represented by atrial data when an analysis of the ventricle data indicates the atrial data may be distorted.

12. A defibrillator or other heart monitoring device in accordance with claim 1 wherein only the correlated subset of transform components are computed.

13. A defibrillator or other heart monitoring device in accordance with claim 1 wherein the discrete wavelet transformation is the Haar transformation, where the number of digital data samples is an even power of two, and where a fast version of the Haar transformation is utilized.

14. A defibrillator or other heart monitoring device in accordance with claim 13 wherein only those sub-computations of the fast version of the Haar transformation essential to the computation of the correlated subset of components are carried out.

15. A defibrillator or other heart monitoring device in accordance with claim 1 wherein the template contains at least a subset of discrete wavelet transform components, each such component in the template being a median or average or other similarly-computed value selected or computed from multiple corresponding components that each originate in a different one of multiple subsets of components which subsets are each computed from different ones of multiple reference episodes of one of said two different heart rhythms.

16. A defibrillator or other heart monitoring device in accordance with claim 15 wherein groups of heartbeats within such reference episodes are first analyzed to eliminate those groups containing irregular heartbeats, and then a median value for each component is selected from each remaining group in each episode, giving rise to a proto-template for each episode, and then a median value of each component is selected from each episode proto-template, giving rise to the template subset components.

17. A defibrillator or other heart monitoring device in accordance with claim 1 wherein the numeric result of the correlation is compared to a threshold correlation value chosen to give optimum results on reference data, and wherein the correlation value is an indication of whether the numeric result of the correlation is above or below the threshold correlation value.

18. A defibrillator or other heart monitoring device in accordance with claim 17 wherein a time series of multiple correlation output data values are maintained and are continuously examined to see if a number larger than a predetermined threshold number of the most recent correlation output data values are of a particular value, indicating the likely occurrence of a particular one of said two differing heart rhythms.

19. A defibrillator or other heart monitoring device in accordance with claim 18 wherein the predetermined threshold number is set to seven.

20. A defibrillator or other heart monitoring device in accordance with claim 1 wherein the two differing heart rhythms are, respectively, sinus tachycardia and non-sinus tachycardia rhythms originating in the atria.

21. A method for distinguishing two differing heart rhythms comprising the steps of:
capturing electrical representations of a series of sequential heartbeats;
transforming these electrical representations into digital data;
performing mathematical computations including at least a partial discrete wavelet transformation upon the digital data, thereby generating at least a subset of discrete wavelet transformation components corresponding to at least some of the sequential heartbeats chosen such that the components generated and retained include components demonstrated to be suitable for use in distinguishing the two differing heart rhythms and also demonstrated to be relatively low in variability from one heart to another;
providing a corresponding subset of reference discrete wavelet transformation components that are captured from at least one heart beating in accordance with one of the two differing heart rhythms when the electrical representations of heartbeats that gave rise to these components were captured and computed as described above;
correlating each subset of transformation components generated from as described in the "performing" step against the subset of transformation components provided from as described in the "providing" step, giving rise to a sequence of correlation values; and
repeatedly mathematically examining a time sequence of the correlation values to give an indication of whether the first or second of the heart rhythms is present, eliminating isolated instances of heartbeat irregularities and focusing upon longer-term trends in the variation of the heart rhythm as indicated by the correlation values.

22. A method in accordance with claim 21 wherein the discrete wavelet transformation is the Haar transformation.

23. A method in accordance with claim 22 wherein the digital samples of the electrical representations of each heartbeat are taken centered about the P wave notch.

24. A method in accordance with claim 23 wherein, if the digital samples are numbered such that the sample corresponding to the P wave notch is number 16, then the subset correlated includes one or more of the transformed Haar coefficients 1, 5, 9, and 24.

25. A method in accordance with claim 24 wherein the subset correlated includes all of the transformed coefficients 1, 5, 9, and 24.

26. A method in accordance with claim 24 wherein the subset correlated includes all of the transformed coefficients 1, 5, and 24.

27. A method in accordance with claim 24 wherein the subset correlated includes all of the transformed coefficients 5 and 9, and 24.

28. A method in accordance with claim 21 wherein the method is applied to heartbeat representations captured from the atria.

29. A method in accordance with claim 21 wherein the method is applied to heartbeat representations captured from the ventricles.

30. A method in accordance with claim 21 wherein the performing step includes the step of detecting and eliminating possibly distorted heartbeat representations from participating in further analysis.

31. A method in accordance with claim 30 wherein the performing step is carried out upon atrial data, wherein the detecting step is controlled at least in part by ventricle data and eliminates atrial heartbeat representations data from further analysis when an analysis of ventricle data indicates the atrial data may be distorted.

32. A method in accordance with claim 21 wherein only the correlated subset of transform components are computed.

33. A method in accordance with claim 21 wherein the discrete wavelet transformation performed by the performing step is the Haar transformation, wherein the number of digital data samples transformed is an even power of two, and wherein a fast version of the Haar transformation is utilized.

34. A method in accordance with claim 33 wherein only those sub-computations of the fast version of the Haar transformation essential to the computation of the correlated subset of components are carried out.

35. A method in accordance with claim 21 wherein the corresponding subset of reference discrete wavelet transform components includes components each of which is a median or average or other similarly-computed value selected or computed from multiple corresponding components each originating in a different one of multiple subsets of components which are each computed from differing ones of multiple episodes of one of said two different heart rhythms.

36. A method in accordance with claim 35 wherein groups of heartbeats within such episodes are first analyzed to eliminate those groups containing irregular heartbeats, and then a median value for each component is selected from the corresponding components in each remaining group in each episode, thereby giving rise to at least a proto-subset of components for each episode, and then a median value for each component is selected from the corresponding components in each proto-subset, giving rise to at least the corresponding subset of reference discrete wavelet transform components.

37. A method in accordance with claim 21 wherein the correlation values are each produced by comparing the numeric result of each correlation to a threshold correlation value chosen to give optimum results on reference data, such that each correlation value is an indication of whether the numeric result of a correlation is above or below the threshold value.

38. A method in accordance with claim 37 wherein the mathematically examining step includes the steps of maintaining a time series of multiple correlation output data values and then continuously examining this series to see if a number larger than a predetermined threshold number of the most recent correlation output data values are of a particular value, this being taken as an indication of the occurrence of a particular one of said two differing heart rhythms.

39. A method in accordance with claim 38 wherein the predetermined threshold number is set to seven.

40. A method in accordance with claim 21 wherein the two differing heart rhythms are, respectively, sinus tachycardia and non-sinus tachycardia rhythms originating in the atria.

41. An implantable defibrillator or other heart monitoring device designed to distinguish two differing heart rhythms comprising:
electrodes that may be attached to the heart of the recipient of the defibrillator or the patient whose heart is being monitored;
a first electronic mechanism designed to accept electrical representations of individual heartbeat waveforms from the electrodes, transform these electrical representations into digital data, and then perform plural digital filtering operations each focusing upon varying width and varying-positioned windowed portions of each heartbeat waveform to generate a plurality of components, one from each such digital filtering operation, each such component representative of different features of each heartbeat waveform some of which features are spread over the entire width of the waveform and other of which features are concentrated in the varying-width and varying-positioned windowed portions of each waveform, selecting the filtering operations such that the components generated and retained are components determined to be suitable for use in distinguishing the two differing heart rhythms and also determined to be relatively low in the variability of their differing heart rhythm distinguishing capabilities from one recipient or patient to another;
a template containing at least a corresponding subset of components generated as described above from heartbeat waveforms captured from at least one individual whose heart was beating in accordance with one of the two differing heart rhythms when the electrical representations of heartbeats that gave rise to these template components were captured;
a second electronic mechanism for correlating the subset of components provided by the first mechanism against the subset of components provided by the template, giving rise to a correlation value; and a third electronic mechanism for mathematically examining a time series of the correlation values received from the second mechanism and for giving an indication of whether the first or second of the heart rhythm is present, eliminating isolated instances of heartbeat irregularities and focusing upon longer-term trends in the variation of the heart rhythm.

42. A defibrillator or other heart monitoring device in accordance with claim 41 wherein the first mechanism accepts and processes signals of the type originating in the atria.

43. A defibrillator or other heart monitoring device in accordance with claim 41 wherein the first mechanism accepts and processes signals of the type originating in the ventricles.

44. A defibrillator or other heart monitoring device in accordance with claim 41 wherein the first electronic mechanism includes a mechanism for detecting and eliminating possibly distorted heartbeat representations from participating in further analysis.

45. A defibrillator or other heart monitoring device in accordance with claim 44 wherein the first electronic mechanism receives atrial data, and the mechanism for detecting and eliminating receives ventricle data and eliminates heartbeat representations represented by atrial data when analysis of the ventricle data indicates the atrial data may be distorted.

46. A defibrillator or other heart monitoring device in accordance with claim 41 wherein the template contains components, each of which is a median or average or other similarly-computed value selected or computed from multiple corresponding components that each originate in a different one of multiple groups of components which groups are each computed as described above from different ones of multiple reference episodes of one of said two different heart rhythms.

47. A defibrillator or other heart monitoring device in accordance with claim 46 wherein the groups of heartbeats computed from such reference episodes are first analyzed to eliminate those groups containing irregular heartbeats, and then a median compound value is selected from each set of corresponding components in each remaining group of each episode, giving rise to a proto-template of components for each episode, and then a median component value is selected from the corresponding components in the proto-templates, giving rise to the template subset of components.

48. A defibrillator or other heart monitoring device in accordance with claim 41 wherein the numeric result of the correlation is compared to a threshold correlation value chosen to give optimum results on reference data, and wherein the correlation value is an indication of whether the numeric result of the correlation is above or below this threshold value.

49. A defibrillator or other heart monitoring device in accordance with claim 48 wherein a time series of multiple correlation output data values are maintained and continuously examined to see if a number larger than a predetermined threshold number of the most recent correlation output data values are of a particular value, indicating the occurrence of a particular one of said two differing heart rhythms.

50. A defibrillator or other heart monitoring device in accordance with claim 49 wherein this predetermined threshold number is set to seven.

51. A defibrillator or other heart monitoring device in accordance with claim 41 wherein the two differing heart rhythms are, respectively, sinus tachycardia and non-sinus tachycardia generated by the atria.

* * * * *

UNITED STATES PATENT AND TRADEMARK OFFICE
CERTIFICATE OF CORRECTION

| | |
|---|---|
| PATENT NO. | : 7,031,770 B2 |
| APPLICATION NO. | : 10/334651 |
| DATED | : April 18, 2006 |
| INVENTOR(S) | : Collins et al. |

Page 1 of 1

It is certified that error appears in the above-identified patent and that said Letters Patent is hereby corrected as shown below:

On the title page, in "Assistant Examiner", in column 2, line 1, delete "Dana D Green" and insert -- Dana D. Greene --, therefor.

Signed and Sealed this

Thirty-first Day of October, 2006

JON W. DUDAS
*Director of the United States Patent and Trademark Office*